United States Patent [19]

Majoie

[11] 4,238,492

[45] Dec. 9, 1980

[54] PHENOXYALKYLCARBOXYLIC ACIDS

[75] Inventor: Bernard Majoie, Dijon, France

[73] Assignee: Societe de Recherches Industrielles S.O.R.I., Paris, France

[21] Appl. No.: 42,156

[22] Filed: May 24, 1979

[30] Foreign Application Priority Data

May 31, 1978 [GB] United Kingdom ............... 25621/78

[51] Int. Cl.$^3$ ..................... A61K 31/44; C07D 213/79
[52] U.S. Cl. ................................... 424/263; 546/314; 546/315; 560/53; 424/308
[58] Field of Search ................. 546/314, 315; 424/263

[56] References Cited

U.S. PATENT DOCUMENTS

| 3,674,836 | 7/1972 | Creger | 260/473 G |
|---|---|---|---|
| 4,011,232 | 3/1977 | Kathawala | 546/315 |
| 4,064,132 | 12/1977 | Janssen et al. | 546/315 |
| 4,098,908 | 7/1978 | Kathawala | 546/314 |

Primary Examiner—Alan L. Rotman
Attorney, Agent, or Firm—Bacon & Thomas

[57] ABSTRACT

Arylcarbonylphenoxyalkylcarboxylic acids, and alkyl esters and salts thereof, are described. The compounds may be formulated into therapeutic compositions and administered to animals, including humans, for the treatment of hyperlipidaemia and related diseases.

6 Claims, No Drawings

PHENOXYALKYLCARBOXYLIC ACIDS

DESCRIPTION OF INVENTION

This invention relates to derivatives of phenoxyalkylcarboxylic acids which can have useful therapeutic activity, for example as hypolipidaemic and hypocholesterolaemic agents.

The novel derivatives are particularly suitable for the treatment of cardiovascular ailments, especially atheromatic illnesses and illnesses related to a high level of lipids.

The compounds of this invention are of the formula

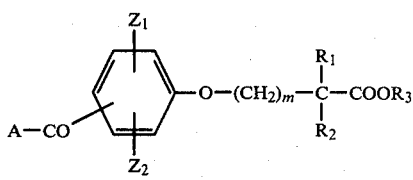

wherein

A is pyridyl, phenyl or phenyl substituted by one, 1 or 3 substituents independently selected from fluorine, chlorine, bromine, trifluoromethyl, nitro, hydroxy, $C_{1-4}$ alkyl and $C_{1-4}$ alkoxy;

$R_1$ and $R_2$ are the same or different and are each hydrogen or methyl;

$R_3$ is hydrogen or $C_{1-4}$ alkyl;

m is an integer of from one to 5;

$Z_1$ and $Z_2$ are the same or different and are each hydrogen, chlorine or methyl; and the A—CO— and —O—$(CH_2)_m$—$CR_1R_2$—$COOR_3$ groups are in the relative meta or para positions.

The present invention also provides the salts of the compounds of formula I, especially (i) the salts obtained by reaction with an organic or inorganic base when $R_3$ is hydrogen, and (ii) the acid addition salts obtained by reaction with an organic or inorganic acid (such as hydrochloric, oxalic, fumaric or maleic acid) when A is 2-pyridyl, 3-pyridyl or 4-pyridyl.

The preferred compounds of this invention are those wherein A is 3-pyridyl, phenyl, phenyl substituted by one or more Cl, Br or F atoms or $CF_3$, $CH_3$ or $OCH_3$ groups (e.g. p-chlorophenyl), m is 3 or 4 and $R_1$ and $R_2$ are each methyl. It is often preferred that $R_3$, $Z_1$ and $Z_2$ are each hydrogen. A is most preferably 3-pyridyl. m is preferably 3 or 4.

A pharmaceutical composition according to the invention comprises a compound or non-toxic salt of the invention in association with a physiologically acceptable excipient. Such compositions can be used for the treatment of cardiovascular ailments.

The compounds of formula I may be prepared by known methods. The preferred method comprises reacting a hydroxyphenyl ketone of the formula

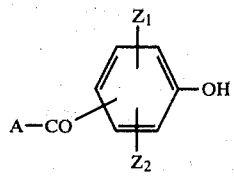

with a halogenated ester of the formula

Hal—$(CH_2)_m$—$CR_1R_2$—$COOR_4$ wherein A, $Z_1$, $Z_2$, m, $R_1$ and $R_2$ are as defined above, Hal is a halogen atom (preferably chlorine or bromine) and $R_4$ is $C_{1-4}$ alkyl (preferably methyl, ethyl, propyl, isopropyl, butyl, isobutyl or tert-butyl) in an anhydrous solvent (preferably dimethylformamide) in the presence of an alkali metal carbonate (preferably $K_2CO_3$), to obtain a compound of formula I in which $R_3$ is $C_{1-4}$ alkyl. This ester may be hydrolysed, if desired, to give the corresponding acid where $R_3$ is hydrogen.

The following non-limitative Examples illustrate how compounds of formula I may be prepared. DMF means dimethylformamide.

EXAMPLE 1

Methyl 5-[4-(p-chlorobenzoyl)phenoxy]-2,2-dimethylpentanoate.

116 g (0.5 mole) of 4'-chloro-4-hydroxybenzophenone, 84 g (0.6 mole) of potassium carbonate and 500 cm³ of DMF are placed in a 1 liter flask. The mixture is brought to reflux and 90 g (0.5 mole) of methyl 5-chloro-2,2-dimethylpentanoate in 200 cm³ of DMF are then added from a dropping funnel. Reflux is continued for 3 hours. The mixture is then cooled and poured into 1 liter of water, so that the desired product precipitates. The precipitate is extracted with diethyl ether, washed with aqueous soda, then with water, dried and decolourised, and the solvent is evaporated under vacuum. 160 g of a white solid are obtained, which are recrystallised from diisopropyl ether. 130 g of the desired product are obtained, m.pt. 64° C.

Analysis: Calcd C,67.29%; H,6.18%. Found C,67.37%; H,6.29%.

EXAMPLE 2

5-[4-(p-chlorobenzoyl)phenoxy]-2,2-dimethylpentanoic acid

The ester of Example 1 is saponified with methanol containing soda to give the desired acid, m,pt. 134° C.

Analysis: Calcd C,66.57%; H,5.87%. Found C,66.54%; H,5.81%.

EXAMPLE 3

Methyl 5-[4-(p-chlorobenzoyl)-3,5-dimethylphenoxy]-2,2-dimethylpentanoate.

Following the procedure of Example 1, but using 4'-chloro-3,5-dimethyl-4-hydroxybenzophenone as the starting ketone, the desired product is obtained as an oil in 71% yield.

EXAMPLE 4

5-[4-(p-chlorobenzoyl)-3,5-dimethylphenoxy]-2,2-dimethylpentanoic acid.

The ester of Example 3 is saponified with methanol containing soda to give the desired acid, m.pt 135° C.

Analysis: Calcd C,67.94%; H,6.48%. Found C,67.69%; H,6.40%.

Table I records a number of products of formula I (in which $R_1$ and $R_2$ are each methyl) which have been prepared following the general procedure of the preceding Examples. The positions of the A—CO, $Z_1$ and $Z_2$ groups are given with respect to the —O—$(CH_2$-

$)_m$—$CR_1R_2$—$COOR_3$ group being arbitrarily defined as at the 1-position of the benzene ring. For instance, in Example 3, A is 4-(p-chlorophenyl), $Z_1$ is 3-$CH_3$ and $Z_2$ is 5-$CH_3$.

TABLE I

| Example | A | $Z_1$ | $Z_2$ | m | $R_3$ | m.pt. (°C.) |
|---|---|---|---|---|---|---|
| 5 | 4-(p-chlorophenyl) | 2-$CH_3$ | 5-$CH_3$ | 3 | $CH_3$ | (Oil) |
| 6 | 4-(p-chlorophenyl) | 2-$CH_3$ | 5-$CH_3$ | 3 | H | 92 |
| 7 | 4-(p-chlorophenyl) | H | H | 4 | isopropyl | (Oil) |
| 8 | 4-(p-chlorophenyl) | H | H | 4 | H | 107 |
| 9 | 4-(3-pyridyl) | H | H | 3 | $CH_3$ | — |
| 10 | 4-(3-pyridyl) | H | H | 3 | H | 126 |
| 11 | 4-phenyl | 2-Cl | 6-Cl | 4 | $C_2H_5$ | — |
| 12 | 4-phenyl | 2-Cl | 6-Cl | 4 | H | — |
| 13 | 4-(m-trifluoromethyl)phenyl | H | H | 3 | $CH_3$ | 70 |
| 14 | 4-(m-trifluoromethyl)phenyl | H | H | 3 | H | 110 |
| 15 | 4-(p-bromophenyl) | H | H | 3 | $CH_3$ | 80 |
| 16 | 4-(p-bromophenyl) | H | H | 3 | H | 145 |
| 17 | 4-(p-fluorophenyl) | H | H | 4 | isopropyl | (Oil) |
| 18 | 4-(p-fluorophenyl) | H | H | 4 | H | 120 |
| 19 | 3-phenyl | H | H | 3 | $CH_3$ | (Oil) |
| 20 | 3-phenyl | H | H | 3 | H | 90 |
| 21 | 3-(p-chlorophenyl) | H | H | 3 | $CH_3$ | (Oil) |
| 22 | 3-(p-chlorophenyl) | H | H | 3 | H | 86 |
| 23 | 3-(3',4'-dichlorophenyl) | H | H | 4 | $CH_3$ | — |
| 24 | 3-(3',4'-dichlorophenyl) | 2-$CH_3$ | 5-$CH_3$ | 4 | $CH_3$ | — |
| 25 | 3-(p-methoxyphenyl) | H | H | 3 | $C_4H_9$ | — |
| 26 | 3-(m-tolyl) | H | H | 3 | $C_2H_5$ | — |
| 27 | 3-(3-pyridyl) | H | H | 3 | $CH_3$ | — |
| 28 | 3-(3-pyridyl) | H | H | 3 | H | — |

The following is a summary of the phramacological tests which have been carried out.

Male Wistar rats (250 to 300 g in weight) were divided into four groups of 20 animals each (2experimental and 2 control groups). The rats were tested for 15 hours before the beginning of the experiment and throughout the tests. At the beginning of the experiment, the animals received, orally, 50 mg/kg of the tested compound in an aqueous gum suspension (gum arabic at a concentration of 30 g/l in water). The decreases in cholesterol level and of total lipids were measured after 24 and 48 hours from administration and the percentage decrease was calculated by comparison with the control rats (which did not receive the gum suspension). The results are shown in Table II.

TABLE II

| Example No. of Compound | Lipid Variation (%) | | Cholesterol Variation (%) | |
|---|---|---|---|---|
| | 24 Hours | 48 Hours | 24 Hours | 48 Hours |
| 10 | −37 | −53 | −35 | −31 |
| 8 | 0 | −36 | −18.8 | −23.2 |
| 20 | −24.8 | −24 | −18.8 | −23.2 |
| 22 | −35 | −45 | −30 | −25 |

The compounds of the invention may be administered to man, orally or by injection.

In the form of capsules, the active substance is mixed with magnesium stearate, amigel and an excipient such as lactose. After filing, capsules are obtained which may, for example, each contain 200 mg of the active ingredient.

In the form of sweetened or unsweetened tablets, the active substance is mixed with lactose and icing sugar. The mixture is granulated in a fluidised bed and the granules which are obtained are tableted in the presence of magnesium stearate.

In injectable form, a soluble compound of formula I is used, for example a sodium salt, and the aqueous solution of this salt, for example in a concentration of 250 g/l is filtered and lyophilised under sterile conditions. The lyophilisate is introduced into a bottle in an amount of from 200 to 500 mg per bottle, ready for putting in extemporaneous solution, with sterile physiological serum, e.g. an aqueous solution of sodium chloride at a concentration of, say, 5 g/l.

Clinically, good results can be obtained with patients suffering from hyperlipidaemia by the administration of 200 to 500 mg daily of a compound of the invention over 20 hours. The most interesting products from a therapeutic view point are those of Table II and the most effective among these compounds are the products of Examples 8 and 22.

I claim:

1. A compound selected from the group consisting of those of formula I

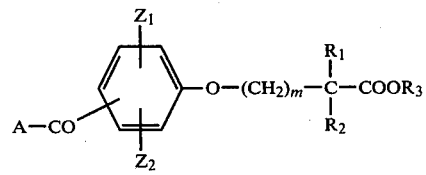

wherein
A is 3-pyridyl; $R_1$ and $R_2$ are the same or different and are each selected from the group consisting of hydrogen and methyl;
$R_3$ is selected from the group consisting of hydrogen or $C_{1-4}$ alkyl;
m is 3 or 4;
$Z_1$ and $Z_2$ are the same or different and are each selected from the group consisting of hydrogen, chlorine and methyl; and
The A—CO— and —O—$(CH_2)_m$—$CR_1R_2$—$COOR_3$ groups are in the relative meta or para positions; and non-toxic salts thereof.

2. A compound of claim 1 wherein $R_1$ and $R_2$ are each methyl.

3. A compound of claim 1 which is 5-(4-nicotinoylphenoxy)-2,2-dimethylpentanoic acid.

4. A therapeutic composition useful in the treatment of hyperlipidaemia which comprises a therapeutically effective amount of a compound or salt of claim 1 and a physiologically acceptable excipient.

5. A compound as defined in claim 1 wherein A is 3-pyridyl, m is 3, $Z_1$ and $Z_2$ each are hydrogen and $R_1$ and $R_2$ each are methyl.

6. A method for treating hyperlipidaemia which comprises administering to a patient suffering from hyperlipidaemia a therapeutically effective amount of a compound or salt of claim 1.

* * * * *